US010137329B2

(12) United States Patent
Gu et al.

(10) Patent No.: US 10,137,329 B2
(45) Date of Patent: Nov. 27, 2018

(54) SMART WALKING RECOMMENDATION APPARATUS AND METHOD (71) Applicant: BOE TECHNOLOGY GROUP CO., LTD., Beijing (CN)

(72) Inventors: Yu Gu, Beijing (CN); Hongli Ding, Beijing (CN); Kai Zhao, Beijing (CN); Ying Zhang, Beijing (CN); Yifei Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/537,700

(22) PCT Filed: May 30, 2016

(86) PCT No.: PCT/CN2016/083918
§ 371 (c)(1),
(2) Date: Jun. 19, 2017

(87) PCT Pub. No.: WO2017/148026
PCT Pub. Date: Sep. 8, 2017

(65) Prior Publication Data
US 2018/0085629 A1  Mar. 29, 2018
US 2018/0296880 A9  Oct. 18, 2018

(30) Foreign Application Priority Data
Mar. 2, 2016 (CN) .......................... 2016 1 0117482

(51) Int. Cl.
*A63B 24/00* (2006.01)
*A61B 5/02* (2006.01)
*G06F 19/00* (2018.01)

(52) U.S. Cl.
CPC .......... *A63B 24/0075* (2013.01); *A63B 24/00* (2013.01); *A63B 24/0003* (2013.01); *A61B 5/02* (2013.01); *G06F 19/3481* (2013.01)

(58) Field of Classification Search
CPC .......................... A63B 24/0003; G01C 22/006
See application file for complete search history.

(56) References Cited

U.S. PATENT DOCUMENTS

| | | | |
|---|---|---|---|
| 2006/0013351 A1* | 1/2006 | Crider | G01C 22/006 377/24.2 |
| 2006/0099556 A1* | 5/2006 | Yeo | A63B 24/0003 434/247 |
| 2006/0136173 A1* | 6/2006 | Case, Jr. | A63B 24/00 702/182 |

FOREIGN PATENT DOCUMENTS

| | | |
|---|---|---|
| CN | 1199487 A | 11/1998 |
| CN | 102200443 A | 9/2011 |

(Continued)

OTHER PUBLICATIONS

English Translation of PCT (CN) International Search Report, Application No. PCT/CN2016/083918, dated Nov. 21, 2016, 3 pps.

(Continued)

*Primary Examiner* — Fabricio R Murillo Garcia
(74) *Attorney, Agent, or Firm* — Armstrong Teasdale LLP (57) ABSTRACT The present disclosure provides a smart walking recommendation apparatus and a corresponding method, the apparatus includes an information obtaining module configured to obtain destination information and appointed arrival time information, a positioning module configured to obtain a start position of a user, a central processing module configured to calculate a distance from the start position to a destination based on the start position and the destination information, and determine whether to recommended walking based on the distance from the start position to the (Continued)

destination, an empirical speed, and the appointed arrival time information, and an output module configured output a walking recommendation to the user in response to determining to recommend walking.

20 Claims, 3 Drawing Sheets

(56) References Cited

FOREIGN PATENT DOCUMENTS

| | | |
|---|---|---|
| CN | 102239388 A | 11/2011 |
| CN | 103727948 A | 4/2014 |
| CN | 103812980 A | 5/2014 |
| CN | 105148461 A | 12/2015 |
| CN | 105212909 A | 1/2016 |
| CN | 205360447 U | 7/2016 |
| WO | 2010112469 A1 | 10/2010 |
| WO | 2015164944 A1 | 11/2015 |

OTHER PUBLICATIONS

PCT (CN) International Search Report, Application No. PCT/CN2016/083918, dated Nov. 21, 2016, 3 pps.: with English translation.

China First Office Action, Application No. 201610117482.8, dated Aug. 1, 2017, 9 pps.: with English translation.

\* cited by examiner

SMART WALKING RECOMMENDATION APPARATUS AND METHOD

CROSS REFERENCE TO RELATED APPLICATIONS

This patent application is a National Stage Entry of PCT/CN2016/083918 filed on May 30, 2016, which claims the benefit and priority of Chinese Patent Application No. 201610117482.8 filed on Mar. 2, 2016, the disclosures of which are incorporated by reference herein in their entirety as part of the present application.

BACKGROUND

Embodiments of the present disclosure relate to the field of green travel, and in particular to a smart walking recommendation apparatus and method.

Walking is a fitness exercise with a lot of benefits to people. Studies show that people who walk a lot every day are significantly healthier than those who exercise less. The World Health Organization defines walking as the best sport in the world. Walking a lot every day can not only reduce the pollution caused by driving to the environment, but also exercise the body. However, in practice, in order to avoid lateness, people usually choose to drive or other faster means, because it cannot be accurately estimated how long it will take to reach the destination by walk in the end.

Therefore, there is a need for a smart walking recommendation solution in the art.

BRIEF DESCRIPTION

One aspect of the present disclosure provides a smart walking recommendation apparatus, including an information obtaining module configured to obtain destination information and appointed arrival time information, a positioning module configured to obtain start position of a user, a central processing module configured to calculate a distance from the start position to a destination based on the start position and the destination information, and determine whether to recommend walking based on the distance from the start position to the destination, an empirical speed, and the appointed arrival time information, and an output module configured to output a walking recommendation to the user in response to the central processing module determining to recommend walking.

According to an exemplary embodiment of the present disclosure, the central processing module is further configured to calculate the time $t=s/v_{avg}$ required for the user to reach the destination, where s is the distance from the start position to the destination, $v_{avg}$ is the empirical speed, if $t<t_1-t_0-\varepsilon$, recommend walking, otherwise not to recommend walking, wherein $t_1$ is the appointed arrival time, $t_0$ is the start time, $\varepsilon$ is a pre-specified buffer time value, wherein when the apparatus is used for the first time, the empirical speed $v_{avg}$ is an average speed of a population to which the user belongs, and when the apparatus is used again, the empirical speed $v_{avg}$ is an empirical speed updated based on the user's previous walking data.

According to an exemplary embodiment of the present disclosure, the apparatus further includes a monitoring module configured to monitor the user's health data and current speed in real time after the user has determined to take a walk, the central processing module is further configured to compare the user's health data with normal standard ranges, calculate the remaining distance and time, generate a recommendation for adjusting the speed based on results of the comparison, the current speed, and the remaining distance and time, and the output module is further configured to output the recommendation for adjusting the speed to the user.

According to a further exemplary embodiment of the present disclosure, the monitoring module includes any one or more of a body temperature monitoring unit for monitoring body temperature, a heart rate monitoring unit for monitoring heart rate, a blood oxygen monitoring unit for monitoring blood oxygen, and a blood pressure monitoring unit for monitoring blood pressure.

According to a further exemplary embodiment of the present disclosure, the central processing module is further configured to, if any item of the user's health data deviates from a normal standard range, generate and output through the output module a deceleration recommendation until the user's health data is restored to the normal standard range, and if all the user's health data is in normal standard ranges and the current speed is lower than $$\max\left(v_{avg}, \frac{S_{left}}{t_{left}}\right),$$

generate and output through the output module a recommendation to accelerate up to this speed, where $v_{avg}$ is the empirical speed, $S_{left}$ is the remaining distance, $t_{left}$ is the remaining time.

According to an exemplary embodiment of the present disclosure, the central processing module is further configured to, after the user has finished this walk, update the empirical speed with a weighted average of the empirical speed and an average speed of this walk.

According to a further exemplary embodiment of the present disclosure, if the user's health data has not deviated from normal standard range data during this walk, the average speed of this walk is the distance from the start position to the destination divided by the time spent for this walk. If the user's health data has deviated from normal standard range data m times during this walk, the entire walking process is divided into 2m+1 segments, and the average speed of this walk is a weighted average of the average speeds of every segment in the 2m+1 segments, wherein for the m segments where the user's health data has deviated from normal standard range data, their weights are negatively correlated with the proportion of the user's health data deviating from a normal standard range.

According to an exemplary embodiment of the present disclosure, if the user has failed to reach the destination at the appointed arrival time and the user's health data has not deviated from normal standard range data during this walk, the weight of the empirical speed is greater than the weight of the average speed of this walking. If the user has failed to reach the destination at the appointed arrival time and the user's health data has deviated from normal standard range data during this walk, the weight of the empirical speed is less than the weight of the average speed of this walk.

According to an exemplary embodiment of the present disclosure, if the user has reached the destination at the appointed arrival time, the weight of the empirical speed is equal to the weight of the average speed of this walk.

According to an exemplary embodiment of the present disclosure, the information obtaining module, positioning module, central processing module, monitoring module, and output module are included in a wearable device.

According to an exemplary embodiment of the present disclosure, the information obtaining module includes any one or more of a voice input module, a touch input module, and a key input module, which are respectively configured to obtain the user's destination information and appointed arrival time information by voice, touch, or key input. The positioning module is a satellite positioning module configured to obtain the user's current position by satellite positioning.

According to an exemplary embodiment of the present disclosure, the output module includes any one or more of a display output module and a voice output module, which are respectively configured to output the recommendation to the user by display or voice.

According to an exemplary embodiment of the present disclosure, the central processing module and the monitoring module are included in a wearable device, the information obtaining module, the positioning module, and the output module are included in a mobile terminal device, and the wearable device further includes a communication module for communicating with the mobile terminal device.

Another aspect of the present disclosure provides a smart walking recommendation method, including obtaining destination information and appointed arrival time information, obtaining a start position of a user, calculating a distance from the start position to a destination based on the start position and the destination information, determining whether to recommend walking based on the distance from the start position to the destination, an empirical speed, and the appointed arrival time information, and in response to determining to recommend walking, outputting a walking recommendation to the user.

According to an exemplary embodiment of the present disclosure, determining whether to recommend walking based on the distance from the start position to the destination, an empirical speed, and the appointed arrival time information includes calculating the time $t=s/v_{avg}$ required for the user to reach the destination, where s is the distance from the start position to the destination, $v_{avg}$ is the empirical speed, if $t < t_1 - t_0 - \varepsilon$, recommending walking, otherwise not recommending walking, wherein $t_1$ is the appointed arrival time, $t_0$ is the start time, $\varepsilon$ is a pre-specified buffer time value, wherein when the method is executed for the first time, the empirical speed $v_{avg}$ is an average speed of a population to which the user belongs, and when the method is executed again, the empirical speed $v_{avg}$ is an empirical speed updated based on the user's previous walking data.

According to an exemplary embodiment of the present disclosure, the method further includes monitoring the user's health data and the current speed in real time after the user has determined to take a walk, comparing the user's health data with normal standard ranges, calculating the remaining distance and time, generating a recommendation for adjusting the speed based on results of the comparison, the current speed, and the remaining distance and time, and outputting the recommendation for adjusting the speed to the user.

According to an exemplary embodiment of the present disclosure, the user's health data includes any one or more of body temperature, heart rate, blood oxygen, and blood pressure.

According to an exemplary embodiment of the present disclosure, generating a recommendation for adjusting the speed based on results of the comparison, the current speed, and the remaining distance and time includes, if any item of the user's health data deviates from a normal standard range, generating and outputting to the user a deceleration recommendation until the user's health data is restored to the normal standard range, and if all the user's health data is in normal standard ranges and the current speed is lower than $$\max\left(v_{avg}, \frac{S_{left}}{t_{left}}\right),$$

generating and outputting to the user a recommendation to accelerate up to this speed, where $v_{avg}$ is the empirical speed, $S_{left}$ is the remaining distance, $t_{left}$ is the remaining time.

According to an exemplary embodiment of the present disclosure, the method further includes, after the user has finished this walk, updating the empirical speed with a weighted average of the empirical speed and an average speed of this walk.

According to an exemplary embodiment of the present disclosure, if the user's health data has not deviated from normal standard ranges data during this walk, the average speed of this walk is the distance from the start position to the destination divided by the time spent for this walk. If the user's health data has deviated from the normal standard range data m times on this walk, the entire walking process is divided into 2m+1 segments, and the average speed of this walk is a weighted average of the average speeds of every segment in the 2m+1 segments, wherein for the m segments where the user's health data has deviated from normal standard range data, their weights are negatively correlated with the proportion of the user's health data deviating from the normal standard range.

According to an exemplary embodiment of the present disclosure, if the user has failed to reach the destination at the appointed arrival time and the user's health data has not deviated from normal standard range data during this walk, the weight of the empirical speed is greater than the weight of the average speed of this walk. If the user has failed to reach the destination at the appointed arrival time and the user's health data has deviated from normal standard range data during this walk, the weight of the empirical speed is less than the weight of the average speed of this walk.

According to an exemplary embodiment of the present disclosure, if the user has reached the destination at the appointed arrival time, the weight of the empirical speed is equal to the weight of the average speed of this walk.

Embodiments of the present disclosure provide a smart walking recommendation solution that can accurately estimate the required time based on the user's empirical walking speed, thereby reducing driving, increasing green travel and healthy exercise. In addition, some embodiments of the present disclosure may offer reasonable recommendation for the user's walking states according to the user's health indicators in the course of walking, thus maximizing the exercise effects at the same time of achieving the travel goal, as well as avoiding the risk of health hazards by excessive exercise.

DETAILED DESCRIPTION

In order to provide a better understanding of the solution of the present disclosure by those skilled in the art, the smart walking recommendation apparatus provided in embodiments of the present disclosure will be described in further detail with reference to the accompanying drawings and specific embodiments. Obviously, the described embodiments are part of the present disclosure, not all embodiments. All other embodiments obtained by one of ordinary skill in the art based on the described embodiments of the disclosure without the need for creative work are within the scope of the present disclosure.

The solution of the present disclosure may be embodied as an apparatus and a method. The apparatus may be in the form of a wearable device such as a wristwatch, a bracelet, or an arm ring, which needs to contact the skin in use in order to collect physical health data. The power source of the apparatus may be a battery, such as a lithium battery, a solar cell, or the like.

The apparatus of the present disclosure may have at least two classes of embodiments:

1. The apparatus itself has a display module (e.g., including the screen) and a positioning module (such as a GPS module), and does not rely on a mobile terminal such as a mobile phone to display information and positioning.

2. Accessing through an application (APP) installed on a mobile terminal such as a mobile phone, and using the mobile terminal's display module and positioning module, the apparatus itself does not have a display module and positioning module.

Figure 1:
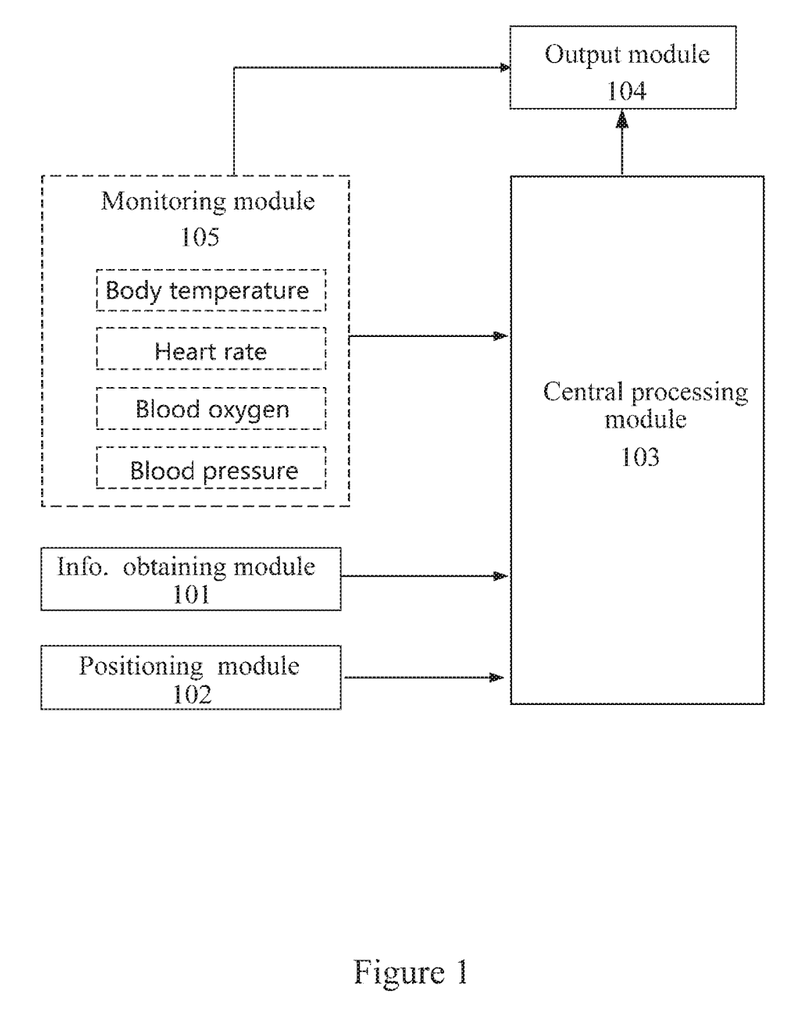
FIG. 1 shows a schematic block diagram of a smart walking recommendation apparatus according to a class of embodiments of the present disclosure.

Embodiments of the present disclosure will be described below with reference to the accompanying drawings. FIG. 1 shows a smart walking recommendation apparatus according to a first class of embodiments of the present disclosure. As shown in FIG. 1, the smart walking recommendation apparatus includes an information obtaining module 101 configured to obtain destination information and appointed arrival time information, a positioning module 102 configured to obtain a start position of a user, a central processing module 103 configured to calculate a distance from the start position to the destination based on the start position and the destination information of the user, and to determine whether to recommend the user walking based on the distance from the start position to the destination, an empirical speed, and the appointed arrival time information, and an output module 104 configured to output a walking recommendation to the user in response to determining to recommend the user walking.

In the first class of embodiments of the present disclosure, the information obtaining module 101, the positioning module 102, the central processing module 103, and the output module 104 are included in a wearable device.

According to an embodiment of the present disclosure, the central processing module 103 may determine whether to recommend the user walking in the following manner: calculating the time $t=s/v_{avg}$ required for the user to arrive at the destination, where s is the distance from the start position to the destination, $v_{avg}$ is an empirical speed, if $t<t_1-t_0-\varepsilon$, recommending the user walking, otherwise not recommending the user walking, where $t_1$ is the appointed arrival time, $t_0$ is the start time, and $\varepsilon$ is a pre-specified buffer time value, wherein when the apparatus is used for the first time, the empirical speed $v_{avg}$ may be an average speed of a population to which the user belongs, and when the apparatus is used again, the empirical speed $v_{avg}$ may be an empirical speed updated based on previous walking data of the user.

For example, when the user first uses the smart walking recommendation apparatus, the user may input information such as his/her age and gender by the information input module 101, and the central processing module 103 may select an average speed of a population to his/her age and gender belong based on the information, as the empirical speed $v_{avg}$. Of course, in this case, the smart walking recommendation apparatus should store in advance the correspondence between populations of different ages and genders, and average speeds.

Each time after the user has used the smart walking recommendation apparatus, the central processing module 103 may update the empirical speed $v_{avg}$, the specific method of which may be as described hereinafter.

The pre-specified buffer time value $\varepsilon$ may be a fixed time value built in the system or a time value that can be set by the user. The value can be any time value greater than or equal to zero.

According to an embodiment of the present disclosure, the smart walking recommendation apparatus further includes a monitoring module 105 configured to monitor the user's health data and current speed in real time after the user has determined to take a walk (the current speed is, for example, the walking speed of the user at each monitoring time during the whole walking process), and the central processing module 103 is further configured to compare the user's health data with normal standard ranges, calculate the remaining distance and time and, based on results of the comparison, the current speed, and the remaining distance and time to obtain a recommendation for adjusting the speed, and the output module 104 is further configured to output the recommendation for adjusting the speed to the user.

According to an embodiment of the present disclosure, the monitoring module 105 includes any one or more of a body temperature monitoring unit, a heart rate monitoring unit, a blood oxygen monitoring unit, and a blood pressure monitoring unit for monitoring body temperature data, heart rate data, blood oxygen data, and blood pressure data.

According to a further embodiment of the disclosure, the central processing module 103 is further configured to: if any item of the user's health data deviates from a normal standard range, generate and output through the output module 104 a deceleration recommendation until the user's health data is restored to the normal standard range, if all the user's health data is in normal standard ranges and the current speed is lower than $$\max\left(v_{avg}, \frac{S_{left}}{t_{left}}\right),$$

generate and output through the output module a recommendation to accelerate up to this speed, where $v_{avg}$ is the empirical speed, $S_{left}$ is the remaining distance, and $t_{left}$ is the remaining time.

The normal standard ranges are, for example, normal ranges of the user's health data such as body temperature, heart rate, blood pressure, blood oxygen, and the like. According to the above-described embodiment, after the user has determined to take a walk, if any item of the user's health data such as body temperature, heart rate, blood pressure, blood oxygen, etc. monitored in real time exceeds a normal range, it is recommended that the user decelerate until the user's health is restored to the normal standard range. If all the user's health data such as body temperature, heart rate, blood pressure, blood oxygen, etc. monitored in real time is within a normal range, and the current speed is lower than the maximum among the empirical speed adopted on this walking recommendation and the ratio between the remaining distance and the remaining time, then it is recommended that the user speed up to this maximum. The current speed may be calculated by the central processing module 103 based on the movement of the current position obtained by the positioning module 102 in real time and the elapsed time, the remaining distance may be calculated by the central processing module 103 based on the current position obtained by the positioning module 102 in real time and the destination information, and the remaining time may be calculated by the central processing module 103 according to the appointed arrival time and the current time.

According to an embodiment of the present disclosure, the information obtaining module 101 may include any one or more of a voice input module, a touch input module, and a key input module, which are configured to obtain, by voice, touch, or key input, respectively, a user's destination information and appointed arrival time information. Accordingly, the central processing module 103 may include means for interpreting speech, touch, and/or key input. For example, in the case where the information obtaining module 101 includes a voice input module, the central processing module 103 may include a voice understanding unit for interpreting the user voice input from the voice input module to obtain the destination information and appointed arrival time information included in the user voice input.

According to an embodiment of the present disclosure, the positioning module 102 may be a satellite positioning module, such as a GPS module, configured to obtain a user's current position by satellite positioning.

According to an embodiment of the present disclosure, the output module 105 may include any one or more of a display output module and a voice output module configured to output the recommendation to a user by display or voice, respectively.

According to an embodiment of the present disclosure, the smart walking recommendation apparatus may further include a storage unit configured to store data such as the empirical speed, the user's health data, the normal standard range data, the user's current position, the current speed, and the like.

According to an embodiment of the present disclosure, the central processing module 103 is further configured to update the empirical speed with a weighted average of the empirical speed and an average speed of this walk after the user has finished this walk.

According to an embodiment of the present disclosure, if the user's health data does not deviate from normal standard range data on this walk, the average speed of this walk is the distance from the start position to the destination divided by the time spent for this walk. If the user's health data has deviated from normal standard range data m times during this walk, the entire walking process is divided into 2m+1 segments (including the m segments where the user's health data deviates from the normal standard range data, and the m+1 segments, before and after these m segments, where the user's health data is normal), and the average speed of this walk is an weighted average of the average speeds of every segment of these 2m+1 segments, wherein for the m segments where the user's health data has deviated from normal standard range data, their weights are negatively correlated with the proportion of the user's health data deviating from a normal standard range (i.e., their weights decrease as the proportion of the user's health data deviating from a normal standard range increases, and their weights increase as the proportion of the user's health data deviating from a normal standard range decreases). The specific relationship between the weights of the m segments where the user's health data deviates from normal standard range data and the proportions of the user's health data deviating from normal standard range may be any negative correlation relationship, such as an exponential function relationship, an inverse proportional function relationship, and the like.

According to an embodiment of the present disclosure, if the user has failed to reach the destination at the appointed arrival time and the user's health data has not deviated from the normal standard range data during this walk, the weight of the empirical speed is greater than the weight of the average speed of this walk. If the user has failed to reach the destination at the appointed arrival time and the user's health data has deviated from the normal standard range data during this walk, the weight of the empirical speed is less than the weight of the average speed of this walk.

According to an embodiment of the present disclosure, if the user has reached the destination at the appointed arrival time, the weight of the empirical speed is equal to the weight of the average speed of this walk.

A specific method of updating the empirical speed according to an embodiment of the present disclosure is described below:

After the user arrives at the destination, the user may choose to confirm arrival by the information input module 101 of the smart walking recommendation apparatus, e.g., by clicking on a display screen of the apparatus or a display screen of a mobile phone, and the central processing module 103 of the smart walking recommendation apparatus may determine whether or not this walking recommendation is successful based on whether or not the time at which the user chooses to confirm arrival is earlier than or equal to the appointed arrival time. If the user has not chosen to confirm arrival, the smart walking recommendation apparatus may monitor the position of the user through the positioning module 102 at the appointed arrival time, and if the user's position is within a range of $\Delta d$ near the destination, it may be determined that the walking recommendation is successful, where $\Delta d$ may be determined according to the positioning accuracy of the positioning module 102 (e.g., a GPS module), otherwise, it may be determined that the walking recommendation has failed.

If the walking recommendation is successful, the central processing module 103 of the smart walking propulsion apparatus may set flag=1, otherwise it may set flag=0.

1. flag=1

(1) If the user does not have abnormal health parameters (i.e., the user's health data deviates from a normal standard range) during the walk, the updated empirical speed (i.e., the empirical speed that will be used on the next walk) may be calculated as follows:

$$v_{avg}(N+1) = w_1 * v_{avg}(N) + w_2 * s/(t-t_0) \qquad (1)$$

where, $v_{avg}(N+1)$ is the updated empirical speed, $v_{avg}(N)$ is the empirical speed used for this walking recommendation, s is the distance of this walk, t is the actual arrival time, $t_0$ is the start time, $w_1$ and $w_2$ are respective weights. In some embodiments, the weights $w_1 = w_2$.

(2) If there have been m times of abnormal health parameters during the walk, the whole walking process will be divided into 2m+1 segments of distance, and the average speed of this walk may be calculated as follows:

$$\bar{v} = \sum_{i=1}^{2m+1} w_i * \frac{\int_{t_{i-1}}^{t_i} v_i dt}{t_i - t_{i-1}} \qquad (2)$$

where $\bar{v}$ is the average speed of this walk, $v_i$ is the average speed of the i-th segment, $t_i$ is the time when the user reaches the end of the i-th segment, and $w_i$ is the weight of the i-th segment. For the m segments where abnormal health parameters have occurred, their weights are negatively correlated with a deviation index $\tau$, that is, the greater the deviation index $\tau$, the smaller the weight, and the smaller the deviation index $\tau$, the greater the weight. The deviation index may be selected as the maximum of the deviations of the body temperature, heart rate, blood oxygen, and blood pressure.

Specifically, for example, the relationship between the weights w of the m segments of walking where there has been an abnormal health parameter and the deviation index $\tau$ may be an exponential function relationship as follows:

$$w = e^{-k\tau} \qquad (3)$$

where k is a tunable parameter that can be set artificially.

Alternatively, the relationship may be an inverse proportional function as follows:

$$w = \frac{k}{\tau} \qquad (4)$$

where k is a tunable parameter that can be set artificially.

For example, the deviation index $\tau$ may be calculated as follows: finding the extreme value of the user's health indication in the current segment of walking (finding the minimum value in this segment if the health indication has deviated from the lowest value of the standard range, finding the maximum value in this segment if the health indication has deviated from the highest value of the standard range), and finding the proportion of the relative deviation of the maximum (minimum) value from the highest (lowest) value of the standard range, which is the deviation index.

$$\tau = \max(\tau_1, \tau_2, \tau_3, \tau_4) \qquad (5)$$

where, $\tau_1$, $\tau_2$, $\tau_3$, $\tau_4$ are the body temperature, heart rate, blood oxygen, and blood pressure deviation indexes respectively.

For the m+1 segments of normal walking, the weights may be calculated as follows:

$$w = \frac{1 - \Sigma w_{abnormal}}{m+1} \qquad (6)$$

In this way, the updated empirical speed may be calculated as follows:

$$v_{avg}(N+1) = w_1 * v_{avg}(N) + w_2 * \bar{v} \qquad (7)$$

in some embodiments, the weights $w_1 = w_2$.

2. flag=0

(1) If there is no physical abnormality, the updated empirical speed is calculated as shown in equation (1):

$$v_{avg}(N+1) = w_1 * v_{avg}(N) + w_2 * s/(t-t_0) \qquad (1)$$

in some embodiments, $w_1 > w_2$.

(2) If there is a physical abnormality, the calculated average speed of this walk and the updated empirical speed are calculated as shown in equations (2) and (7), respectively:

$$\bar{v} = \sum_{i=1}^{2m+1} w_i * \frac{\int_{t_{i-1}}^{t_i} v_i dt}{t_i - t_{i-1}} \qquad (2)$$

$$v_{avg}(N+1) = w_1 * v_{avg}(N) + w_2 * \bar{v} \qquad (7)$$

in some embodiments, $w_1 > w_2$.

Figure 2:
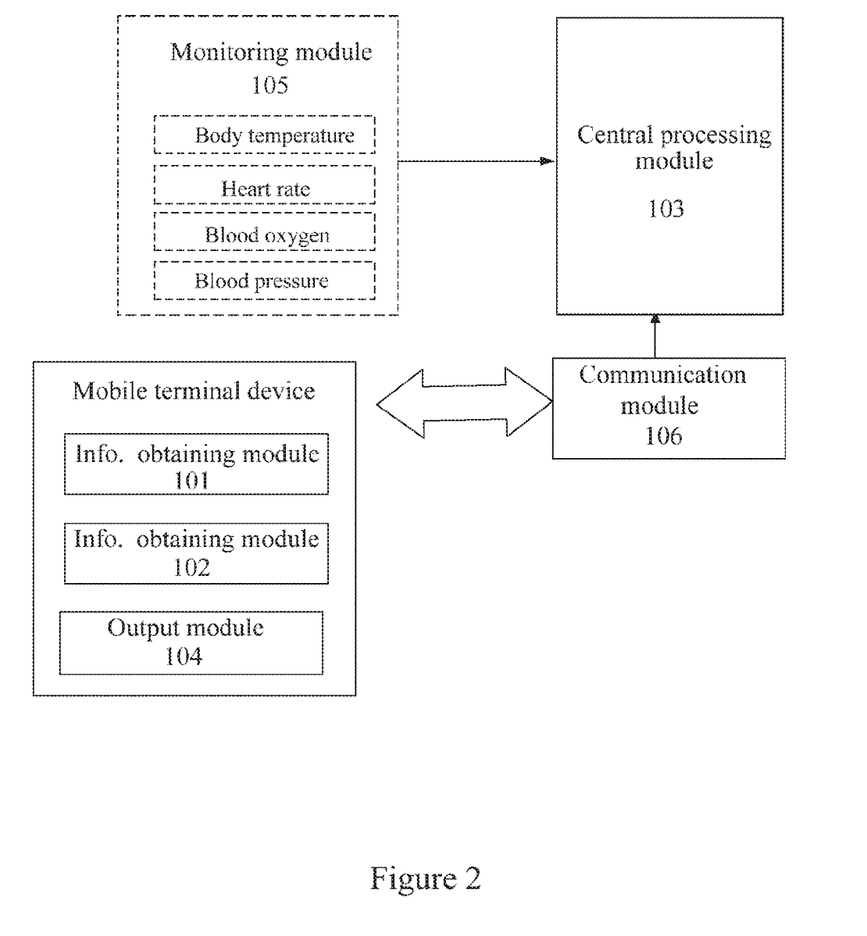
FIG. 2 shows a schematic block diagram of a smart walking recommendation apparatus according to another class of embodiments of the present disclosure.

Referring now to FIG. 2, there is shown a smart walking recommendation apparatus according to a second class of embodiments of the present disclosure. As shown in FIG. 2, the smart walking recommendation apparatus includes an information obtaining module 101, a positioning module 102, a central processing module 103, an output module 104, and a monitoring module 105, wherein the central processing module 103 and the monitoring module 105 are included in a wearable device, the information obtaining module 101, the positioning module 102, and the output module 104 are included in a mobile terminal device, and the wearable device also includes a communication module 106 for communicating with the mobile terminal device.

The mobile terminal device may be a smart phone, a pad, or another mobile terminal device. The information obtaining module 101 may be implemented by an APP on the mobile terminal device to accomplish the input of information such as a destination and an arrival time. The positioning module 102 may be a positioning module (e.g., a GPS module) of the mobile terminal. The output module 104 may be a display or voice output module of a mobile terminal. The communication module 106 may be a Bluetooth communication module, so that communication between the mobile terminal and the smart walking recommendation apparatus of the present disclosure may be realized by Bluetooth. Thus, the pairing of the mobile terminal device with the smart walking recommendation apparatus of the present disclosure may also be performed by Bluetooth. The communication module 106 may also be an NFC communication module, so that communication between the mobile terminal and the smart walking recommendation apparatus of the present disclosure may be achieved by NFC. Thus, the pairing process of the mobile terminal device and the smart walking recommendation apparatus of the present disclosure may also be performed by NFC, for example, by placing the mobile terminal device such as a mobile phone within 20 cm of the smart walking recommendation apparatus of the present disclosure.

The functions of the modules in the smart walking recommendation apparatus according to the second class of embodiments of the present disclosure are similar to the functions of the corresponding modules in the smart walking recommendation apparatus according to the first class of embodiments of the present disclosure, and will not be described again.

The smart walking recommendation apparatus according to embodiments of the present disclosure has been described above with reference to the accompanying drawings, and it is to be noted that the above description is by way of example only and is not intended to limit the present disclosure. In other embodiments of the present disclosure, the apparatus may have more, less, or different modules, and the relationships of connection, containment, function, etc. among the modules may be different from those described and illustrated.

Figure 3:
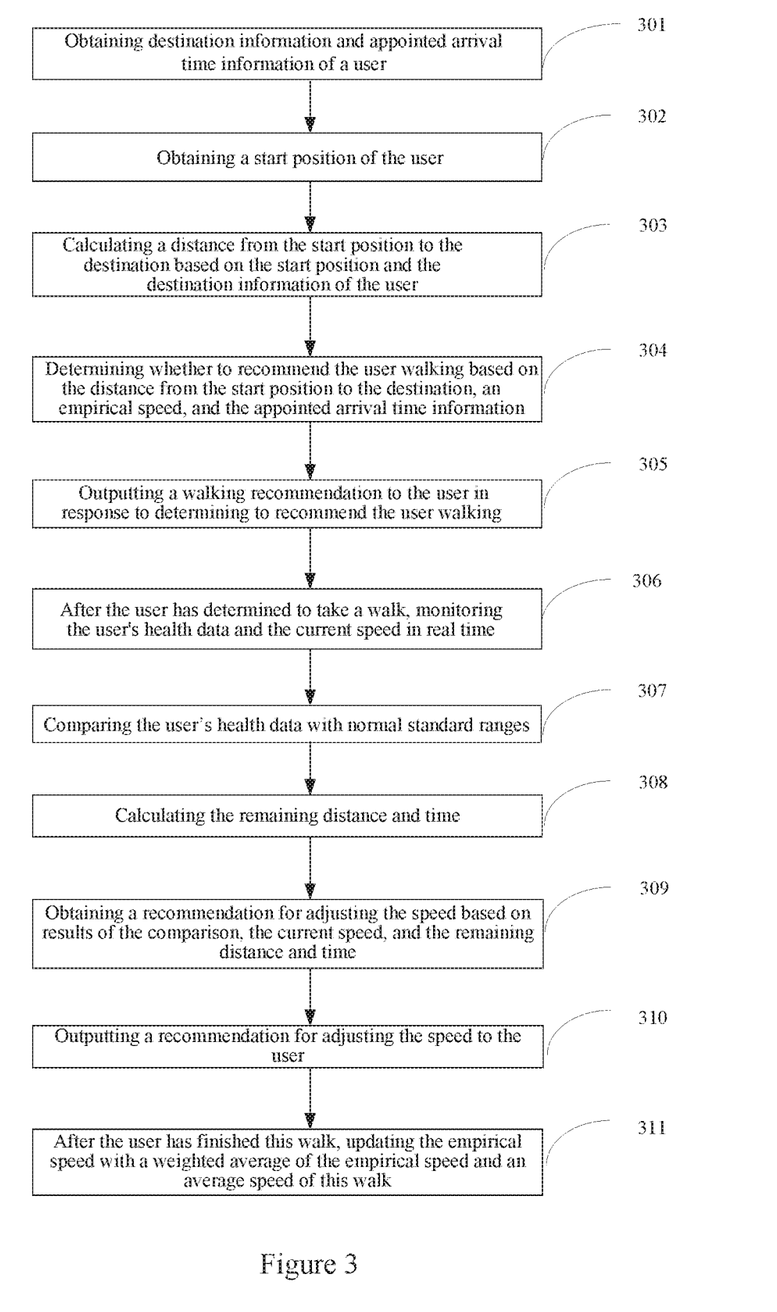
FIG. 3 shows a flow diagram of a smart walking recommendation method according to an embodiment of the present disclosure.

Referring now to FIG. 3, there is shown a smart walking recommendation method according to an embodiment of the present disclosure. The smart walking recommendation method may be executed by the smart walk recommendation apparatus according to an embodiment of the present disclosure after being started, and for the sake of simplicity, some details repeated with the above description are omitted in the following description, and therefore, a more detailed understanding of the method may be had by referring to the above description.

As shown in the figure, the smart walking recommendation method includes the following steps:

Step 301, obtaining destination information and appointed arrival time information of a user;

Step 302, obtaining a start position of the user;

Step 303, calculating a distance from the start position to the destination based on the start position and the destination information of the user;

Step 304, determining whether to recommend the user walking based on the distance from the start position to the destination, an empirical speed, and the appointed arrival time information; and Step 305, outputting a walking recommendation to the user in response to determining to recommend the user walking.

According to an embodiment of the present disclosure, the determining whether to recommend the user walking based on the distance from the start position to the destination, an empirical speed, and the appointed arrival time information includes calculating the time $t=s/v_{avg}$ required for the user to reach the destination, where s is the distance from the start position to the destination, $v_{avg}$ is the empirical speed, if $t<t_1-t_0-\varepsilon$, recommending the user walking, otherwise not recommending the user walking, where $t_1$ is the appointed arrival time, $t_0$ is the start time, $\varepsilon$ is a pre-specified buffer time value, wherein when the method is first executed, the empirical speed $v_{avg}$ is an average speed of a population to which the user belongs, and when the method is executed again, the empirical speed $v_{avg}$ is an empirical speed updated based on the user's previous walking data.

According to an embodiment of the present disclosure, the method further includes the following optional steps:

Step 306, after the user has determined to take a walk, monitoring the user's health data and the current speed in real time;

Step 307, comparing the user's health data with normal standard ranges;

Step 308, calculating the remaining distance and time;

Step 309, obtaining a recommendation for adjusting the speed based on results of the comparison, the current speed, and the remaining distance and time; and Step 310, outputting the recommendation for adjusting the speed to the user.

According to an embodiment of the present disclosure, the user's health data includes any one or more of body temperature data, heart rate data, blood oxygen data, and blood pressure data.

According to an embodiment of the present disclosure, the obtaining a recommendation for adjusting the speed based on results of the comparison, the current speed, and the remaining distance and time include, if any item of the user's health data deviates from a normal standard range, generating and outputting to the user a deceleration recommendation until the user's health data is restored to the normal standard range, if all the user's health data is in normal standard ranges and the current speed is lower than $$\max\left(v_{avg}, \frac{S_{left}}{t_{left}}\right),$$

generating and outputting to the user a recommendation to accelerate up to this speed, where $v_{avg}$ is the empirical speed, $S_{left}$ is the remaining distance, and $t_{left}$ is the remaining time.

According to an embodiment of the present disclosure, the method further includes the following step:

Step 311, after the user has finished this walk, updating the empirical speed with a weighted average of the empirical speed and an average speed of this walk.

According to a further embodiment of the present disclosure, if the user's health data has not deviated from normal standard range data during this walk, the average speed of the this walk is the distance from the start position to the destination divided by the time spent for this walk. If the user's health data has deviated from the normal standard range data m times during this walk, the entire walking process is divided into 2m+1 segments, and the average speed of this walk is a weighted average of the average speeds of every segment in the 2m+1 segments, wherein for the segments where the user's health data has deviated from normal standard range data, their weights are negatively correlated with the proportion of the user's health data deviating from the normal standard range.

According to a still further embodiment of the present disclosure, if the user has failed to reach the destination at the appointed arrival time and the user's health data has not deviated from normal standard range data during this walk, the weight of the empirical speed is greater than the weight of the average speed of this walk, if the user has failed to reach the destination at the appointed arrival time and the user's health data has deviated from normal standard range data during this walk, the weight of the empirical speed is less than the weight of the average speed of this walk.

According to a still further embodiment of the present disclosure, if the user has reached the destination at the appointed arrival time, the weight of the empirical speed is equal to the weight of the average speed of this walk.

The smart walking recommendation method according to embodiments of the present disclosure has been described above with reference to the accompanying drawings, and it should be noted that the above description is merely an example and is not a limitation of the smart walking recommendation method of the present disclosure. In other embodiments of the present disclosure, the method may have more, fewer or different steps, the steps may be combined, split, adjusted in order, and the like.

It is to be understood that the above embodiments of the present disclosure are merely exemplary embodiments for explaining the principles of the present disclosure, and the present disclosure is not limited thereto. It will be apparent to those skilled in the art that various changes and modifications may be made therein without departing from the spirit and essence of the disclosure, which changes and modifications are also intended to be within the scope of the present disclosure. The scope of the disclosure is defined only by the language expression of the appended claims and their equivalents.

What is claimed is:

1. A smart walking recommendation apparatus, comprising:
an information obtaining module configured to obtain destination information and appointed arrival time information;
a positioning module configured to obtain a start position of a user;
a central processing module configured to:
calculate a distance for a selected walk from the start position to a destination based on the start position and the destination information; and
determine whether to recommend walking the selected walk based on the distance from the start position to the destination, an empirical speed, and the appointed arrival time information, wherein the empirical speed is updated based on the user's health data associated with previous walks, and deviations in said user's health data from normal standard range data; and
an output module configured to output a walking recommendation to the user in response to the central processing module determining to recommend walking the selected walk.

2. The apparatus according to claim 1, wherein the central processing module is further configured to:
calculate a time $t=s/v_{avg}$ required for the user to reach the destination, where s is the distance from the start position to the destination, and $v_{avg}$ is the empirical speed; and
if $t<t_1-t_0-\varepsilon$, recommend walking the selected walk, otherwise not to recommend walking the selected walk, where $t_1$ is the appointed arrival time, $t_0$ is start time, and $\varepsilon$ is a pre-specified buffer time value;
wherein when the apparatus is used for a first time, the empirical speed $v_{avg}$ is an average speed of a population to which the user belongs, and when the apparatus is used again, the empirical speed $v_{avg}$ is an empirical speed updated based on the user's previous walking data from the previous walks.

3. The apparatus according to claim 1, further comprising:
a monitoring module configured to monitor the user's health data and current speed in real time after the user has determined to take the selected walk, wherein the central processing module is further configured to:
compare the user's health data with normal standard ranges;
calculate the remaining distance and time; and
generate a recommendation for adjusting the speed based on results of the comparison, the current speed, and the remaining distance and time; and wherein
the output module is further configured to output the recommendation for adjusting the speed to the user.

4. The apparatus according to claim 3, wherein the monitoring module comprises at least one of a body temperature monitoring unit for monitoring body temperature, a heart rate monitoring unit for monitoring heart rate, a blood oxygen monitoring unit for monitoring blood oxygen, and a blood pressure monitoring unit for monitoring blood pressure.

5. The apparatus according to claim 3, wherein the central processing module is further configured to:
if any item of the user's health data deviates from a normal standard range, generate and output through the output module a deceleration recommendation until the user's health data is restored to the normal standard range; and
if all the user's health data is in normal standard ranges and the current speed is lower than $$\max\left(v_{avg}, \frac{S_{left}}{t_{left}}\right),$$

generate and output through the output module a recommendation to accelerate up to this speed, where $v_{avg}$ is the empirical speed, $S_{left}$ is the remaining distance, and $t_{left}$ is the remaining time.

6. The apparatus according to claim 3, wherein the information obtaining module, positioning module, central processing module, monitoring module, and output module are included in a wearable device.

7. The apparatus according to claim 3, wherein:
the information obtaining module includes at least one of a voice input module, a touch input module, and a key input module, which are respectively configured to obtain the user's destination information and appointed arrival time information by voice, touch, and key input; and
the positioning module is a satellite positioning module configured to obtain the user's current position by satellite positioning.

8. The apparatus according to claim 3, wherein the output module comprises:
at least one of a display output module and a voice output module, which are respectively configured to output the recommendation to the user by display and voice.

9. The apparatus according to claim 3, wherein the central processing module and the monitoring module are included in a wearable device, wherein the information obtaining module, the positioning module, and the output module are included in a mobile terminal device, and wherein the wearable device further comprises a communication module for communicating with the mobile terminal device.

10. The apparatus according to claim 1, wherein the central processing module is further configured to:
after the user has finished the selected walk, update the empirical speed with a weighted average of the empirical speed and an average speed of the selected walk.

11. The apparatus according to claim 10, wherein:
if the user's health data has not deviated from normal standard range data during the selected walk, the average speed of the selected walk is the distance from the start position to the destination divided by the time spent for the selected walk; and
if the user's health data has deviated from normal standard range data m times during the selected walk, the entire walking process is divided into 2m+1 segments, and the average speed of the selected walk is a weighted average of the average speeds of every segment in the 2m+1 segments, wherein for the m segments where the user's health data has deviated from normal standard range data, their weights are negatively correlated with the proportion of the user's health data deviating from a normal standard range.

12. The apparatus according to claim 10, wherein:
if the user has failed to reach the destination at the appointed arrival time and the user's health data has not deviated from normal standard range data during the selected walk, the weight of the empirical speed is greater than the weight of the average speed of the selected walk; and if the user has failed to reach the destination at the appointed arrival time and the user's health data has deviated from normal standard range data during the selected walk, the weight of the empirical speed is less than the weight of the average speed of the selected walk.

13. The apparatus according to claim 10, wherein if the user has reached the destination at the appointed arrival time, the weight of the empirical speed is equal to the weight of the average speed of the selected walk.

14. A smart walking recommendation method, comprising:
obtaining destination information and appointed arrival time information;
obtaining a start position of a user;
calculating a distance for a selected walk from the start position to a destination based on the start position and the destination information;
determining whether to recommend walking the selected walk based on the distance from the start position to the destination, an empirical speed, and the appointed arrival time information, wherein the empirical speed is updated based on the user's health data associated with previous walks, and deviations in said user's health data from normal standard range data; and
in response to determining to recommend walking the selected walk, outputting a walking recommendation to the user.

15. The method according to claim 14, wherein determining whether to recommend walking based on the distance from the start position to the destination, an empirical speed, and the appointed arrival time information comprises:
calculating a time $t=s/v_{avg}$ required for the user to reach the destination, where s is the distance from the start position to the destination, and $v_{avg}$ is the empirical speed; and
if $t < t_1 - t_0 - \varepsilon$, recommending the user walking the selected walk, otherwise not recommending walking, where $t_1$ is the appointed arrival time, $t_0$ is start time, and $\varepsilon$ is a pre-specified buffer time value;
wherein when the method is executed for a first time, the empirical speed $v_{avg}$ is an average speed of a population to which the user belongs, and when the method is executed again, the empirical speed $v_{avg}$ is an empirical speed updated based on the user's previous walking data from the previous walks.

16. The method according to claim 14, further comprising:
monitoring the user's health data and the current speed in real time after the user has determined to take the selected walk;
comparing the user's health data with normal standard ranges;
calculating the remaining distance and time;
generating a recommendation for adjusting the speed based on results of the comparison, the current speed, and the remaining distance and time; and
outputting the recommendation for adjusting the speed to the user.

17. The method according to claim 16, wherein generating a recommendation for adjusting the speed based on results of the comparison, the current speed, and the remaining distance and time comprises:
if any item of the user's health data deviates from a normal standard range, generating and outputting to the user a deceleration recommendation until the user's health data is restored to the normal standard range; and
if all the user's health data is in normal standard ranges and the current speed is lower than $$\max\left(v_{avg}, \frac{S_{left}}{t_{left}}\right),$$

generating and outputting to the user a recommendation to accelerate up to this speed, where $v_{avg}$ is the empirical speed, $S_{left}$ is the remaining distance, and $t_{left}$ is the remaining time.

18. The method according to claim 14, further comprising:
after the user has finished the selected walk, updating the empirical speed with a weighted average of the empirical speed and an average speed of the selected walk.

19. The method according to claim 18, wherein:
if the user's health data has not deviated from normal standard ranges data during the selected walk, the average speed of the selected walk is the distance from the start position to the destination divided by the time spent for the selected walk; and
if the user's health data has deviated from the normal standard range data m times during the selected walk, the entire walking process is divided into 2m+1 segments, and the average speed of the selected walk is a weighted average of the average speeds of every segment in the 2m+1 segments, wherein for the m segments where the user's health data has deviated from normal standard range data, their weights are negatively correlated with the proportion of the user's health data deviating from the normal standard range.

20. The method according to claim 18, wherein:
if the user has failed to reach the destination at the appointed arrival time and the user's health data has not deviated from normal standard range data during the selected walk, the weight of the empirical speed is greater than the weight of the average speed of the selected walk; and
if the user has failed to reach the destination at the appointed arrival time and the user's health data has deviated from normal standard range data during the selected walk, the weight of the empirical speed is less than the weight of the average speed of the selected walk.

* * * * *